United States Patent [19]

Kasal et al.

[11] Patent Number: 5,141,853

[45] Date of Patent: Aug. 25, 1992

[54] DETERMINATION OF AMMONIA LEVELS IN A SAMPLE

[75] Inventors: Charles A. Kasal, Bedford; Harold M. Tinberg, Dallas; Obaid Hissami, Grapevine, all of Tex.; David A. Yost, Round Lake Park, Ill.

[73] Assignee: Abbott Laboratories, Abbott Park, Ill.

[21] Appl. No.: 223,056

[22] Filed: Jul. 22, 1988

[51] Int. Cl.⁵ ............................................. C12Q 1/32
[52] U.S. Cl. ........................................ 435/26; 435/25
[58] Field of Search ........................ 435/810, 188, 26

[56] References Cited

U.S. PATENT DOCUMENTS

| | | | |
|---|---|---|---|
| 3,929,581 | 12/1985 | da Fonseca-Wollheim | 435/26 |
| 4,266,022 | 5/1981 | Lamprecht | 435/26 |
| 4,672,045 | 6/1987 | Tsutsui | 436/518 |
| 4,764,466 | 4/1988 | Suyama et al. | 435/188 |
| 4,914,040 | 4/1990 | Lenz et al. | 436/512 |

OTHER PUBLICATIONS

Lee, H.-J., et al., *Biochem. J.*, 245:407–414, 1987.
Moysesyan et al., Ref. Zh. Biol. Khim., Abstr. No. 16Ts107, 13:228, 1978.
Stryer, Biochemistry, (2nd Ed.), W. H. Freeman and Co., San Francisco: pp. 408, 487, 1981.
Dolphin et al., ed., *Coenzymes and Cofactors*, Part A, John Wiley & Sons: New York, pp. 570–586, 1987.

*Primary Examiner*—Sam Rosen
*Attorney, Agent, or Firm*—Daniel W. Collins

[57] ABSTRACT

A method and kit for determining the amount of ammonia in a body fluid. The method and kit involve contacting the fluid with glutamate dehydrogenase, alpha-ketoglutarate and nicotinamide hypoxanthine dinucleotide phosphate and determining the amount of ammonia present in the fluid.

18 Claims, 3 Drawing Sheets

DETERMINATION OF AMMONIA LEVELS IN A SAMPLE

BACKGROUND OF THE INVENTION

The present invention relates to a method for determining the amount of ammonia in a body fluid and other samples and to a kit containing the reagents used to perform the method.

The determination of blood ammonia is important in the clinical diagnosis of a number of pathological conditions Elevated ammonia levels are associated with liver diseases, hepatic coma, Reye's syndrome, cardiac failure, and erythroblastosis fetalis. Monitoring of ammonia levels is also useful in the clinical management of patients who have undergone liver transplantation and hyperalimentation.

Determination of levels of ammonia in samples is also done in various industries ranging from the chemical to the food industries. Samples of chemicals, raw materials such as fertilizers and foodstuffs such as bakery goods or fruit juices are regularly analyzed.

Previous methods for the clinical determination of ammonia generally involved titrimetric or photometric analysis of ammonia following the conversion of ammonium ions to volatile form. Difficulties were encountered when systems contained volatile components other than ammonia. In addition, the assay conditions under which ammonia was determined could promote deamidation and deamination reactions, producing inaccurate results. For example, colorimetric determination of ammonia by the Berthelot reaction requires the deproteinization of the sample prior to analysis. Deproteinization, a process carried out at acid pH, can produce ammonia in situ, giving an erroneously high ammonia value.

The introduction of enzymatic methods for the determination of ammonia obviated the disadvantages described above. [see Scand. J. Clin. Lab. Invest., 16 (1964)443]. Such enzymatic systems utilized excess alpha-ketoqlutarate, nicotinamide adenine dinucleotide (NADH), and L-qlutamic dehydrogenase (GLDH). In such an enzymatic system, ammonia is contacted with alpha ketoqlutarate to form qlutamate, with concommitant oxidation of NADH to NAD. The decrease in NADH is directly related to the concentration of ammonia in the sample, and can be conveniently measured by determining the decrease in absorbance of NADH at 340nm.

In the clinical chemistry laboratory, early enzymatic methods utilized acid deproteinized whole blood as samples As described above, such deproteinization can produce an erroneously high ammonia value, affecting the accuracy of the determination. Mondzac et al. [see J. Lab. Clin. Med. 66 (1965)526] described an improved GLDH method which utilized heparinized plasma instead of deproteinized samples. A disadvantage of this method is that a true endpoint does not appear to exist, because other plasma components, such as enzymes, react with NADH. To circumvent this, protracted pre incubation periods of 15-20 minutes were utilized to pre-react these crossreactinq materials. However, such pre-incubation did not totally eliminate these crossreactions.

U.S. Pat. No. 3,929,581 describes an enzymatic method which is an improvement over Mondzac and which is indicated to be free from the disadvantages of earlier procedures. The '581 patent teaches use of non-deproteinized plasma as the sample. The sample is contacted with reduced nicotinamide adenine dinucleotide phosphate (NADPH) and GLDH. In addition, adenosine diphosphate (ADP) is included to stabilize GLDH and accelerate the enzymatic reaction. The patentee reports that the assay takes approximately 5 minutes to perform, which is partially due to the fact that no pre-incubation period is needed. These factors combine to yield an assay essentially free of crossreactions and is therefore specific for ammonia.

The patentee argued that the use of NADPH in the place of NADH was not an obvious substitution of one nicotinamide adenine dinucleotide compound for another. Because of the cross reactivity problems seen with the use of NADH, the same were expected to occur with NADPH. It was also taught that GLDH reacted with NADH much more quickly than with NADPH, and that more undesired slow reaction would occur with the NADPH. However, neither of these problems arose with the method of '581.

An objective of this invention is to provide an alternative testing method for blood ammonia levels without the need for deproteinization and without the use of NADH. Another objective is the development of a blood ammonia assay that can be performed rapidly enough to be used on an automated diagnostic system. In particular, another objective of this invention is to provide for reagent test kits that can be used in automated diagnostic systems to test for blood ammonia.

SUMMARY OF THE INVENTION

The present invention is a method and a kit that is used for determining the amount of ammonia in a sample. The method involves contacting the sample with GLDH, alpha-ketoglutarate, and reduced nicotinamide hypoxanthine dinucleotide phosphate (NHxDPH) and determining therefrom the amount of ammonia present in the sample.

The reagents used in the inventive method can be combined in a kit form wherein the components of the kit, qlutamate dehydrogenase/alpha-ketoqlutarate, NHxDPH and buffer, can be packaged separately and easily combined to be used as the reagent system in the claimed method. In particular, the reagents can also be readily adapted to automated diagnostic systems, thereby insuring the reproducibility and the accuracy of the test.

DETAILED DESCRIPTION OF THE INVENTION

The present invention is directed to a method and a kit to determine the amount of ammonia present in a sample. The method comprises contacting said sample with GLDH, alpha-ketoglutarate and NHxDPH for a time sufficient to consume the ammonia present and to oxidize NHxDPH to NHxDP, measuring the absorbance change through spectrophotometric or other means and determining therefrom the amount of ammonia present the sample. The reaction is further described as follows:

$NH_4^+$ + alpha-ketoglutarate +

Figure 1:
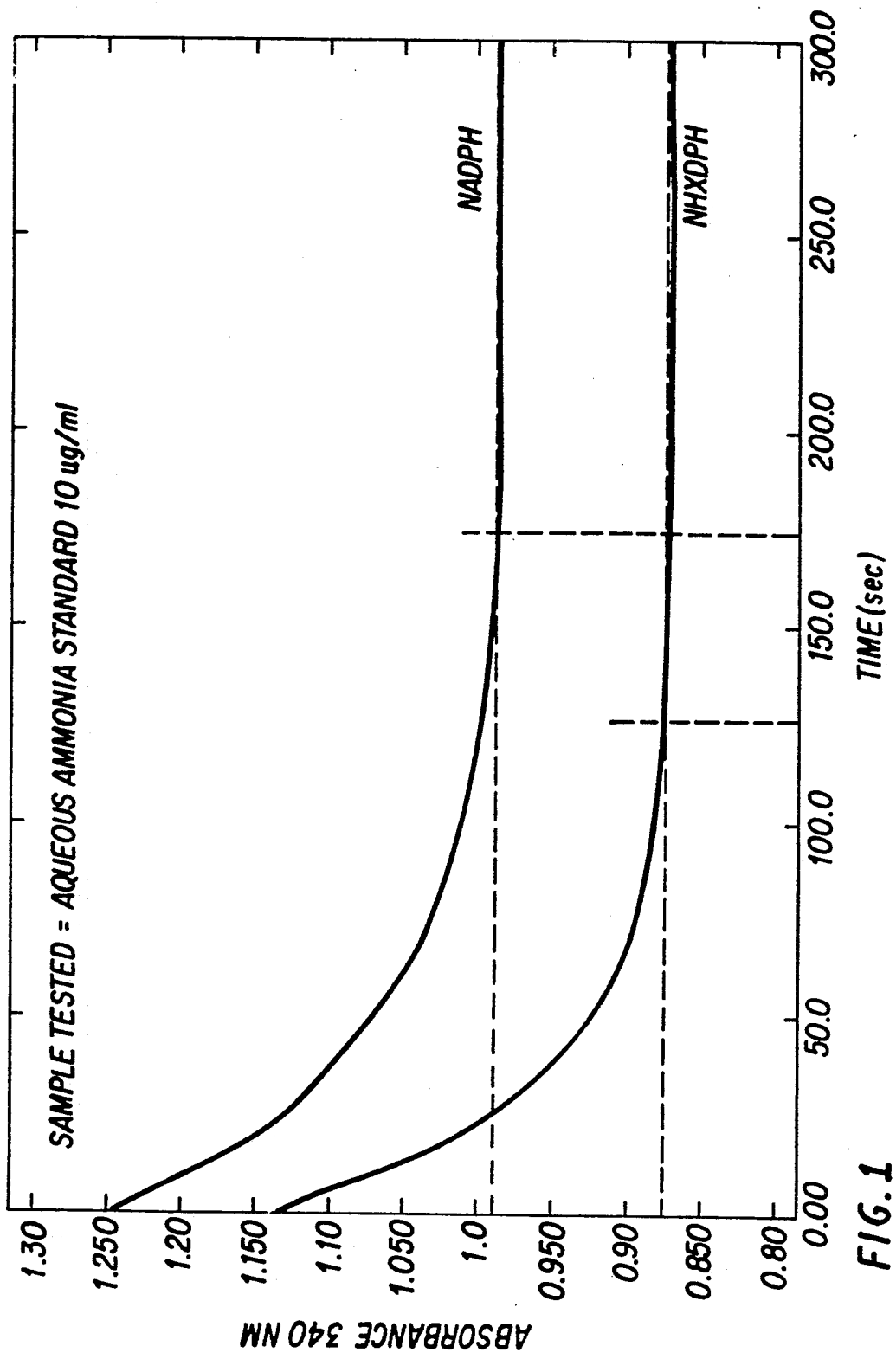

In comparison to reagent systems containing NADPH, reagents formulated with NHxDPH reached endpoint faster, thereby providing a more efficient reaction system. As shown in FIG. 1, aqueous standards at 10 micrograms/ml (w/v) of ammonia were run using the claimed method. A comparative series of tests was conducted wherein the same method was used, but NADPH replaced NHxDPH. The NADPH reaction reached equilibrium and a stable endpoint at approximately 175 seconds or about three minutes. The method containing NHxDPH reached equilibrium at approximately 125 seconds, or about one minute sooner.

This increase in the reaction rate is especially important when the inventive method is used in automated diagnostic systems. For example, the Abbott Spectrum High Performance Diagnostic System ® (Abbott Laboratories, Abbott Park, IL) is a random access analytic system which performs a variety of diagnostic assays and whose efficiency depends on the total reaction time of scheduled tests. Short reaction times dramatically increase sample throughput.

This increased rate of reaction through the use of NHxDPH instead of NADPH was unexpected simply based on the structural similarities between the two dinucleotide phosphates, and especially since in some cases, the opposite has been observed. For example, Stone et al. [see Biochem. 23(1984) 4340] reported that in the case of the enzyme dihydrofolate reductase, NHxDPH reacted more slowly that NADPH.

The sample is selected from the group consisting of plasma, serum, urine or other body fluids. It is also anticipated that, although the inventive process is particularly suitable for biological samples, it can be used or adapted for use with samples obtained from industrial or commercial uses, such as raw materials for chemical processes, chemical products and foodstuffs.

The method of the present invention is carried out at a neutral to mildly alkaline pH since the activity of the GLDH is optimal in this pH range. This pH range lies from about pH 6 to about pH 9.5 and is preferably from about 8 to 9. It is particularly preferable to perform this assay in the slightly alkaline range of from about pH 8.3 to about 8.5 and especially at pH 8.4. A tris (hydroxymethyl) aminomethane buffer is used to keep the pH within the alkaline range, however, other suitable buffers or buffer systems may be used, such as phosphate buffer and triethanolamine buffer.

The concentration of the GLDH in the reagent formulation is at least 1 U/ml (Units of activity/ml) and the alpha-ketoqlutarate concentration in the reaction mixture is at least 1 mM. The concentration of NHxDPH is in the range of from about 0.05 to about 0.5.mM.

Optionally, a stabilizer can be used to stabilize the body fluid sample, in particular, blood, plasma, and serum matrices components. The stabilizer can be a mixture of surfactant and dextran sulfate and is preferably a mixture of polyoxyethylene lauryl ether with 23 moles of ethylene oxide and dextran sulfate at an average molecular weight of approximately 500,00. The claimed method can be performed in at least two different ways. Example 1 below is a one-step ammonia test where ammonia standard samples were tested. Example 2 is another configuration of the inventive method Example 3 determines the correlation of the inventive method to a known method.

EXAMPLE 1

Components 1, 2, and 3, consisting of the were prepared.

Component 1

4 mg/ml NHxDPH
50% propylene glycol
1 mg/ml (w/v) sodium azide
3.1 mg/ml (w/v) boric acid
16 mg/ml (w/v) bicine buffer
pH at 10.2

Component 2

16 mg/ml (w/v) alpha-ketoqlutarate
572 U/ml qlutamate dehydrogenase
0.05 M phosphate buffer at pH 7.0 to 7.4
33% glycerol (v/v)
0.05 mg/ml (w/v) bovine gamma globulin
0.5 mg/ml (w/v) sodium azide Component 3

2.6 mM alpha ketoqlutarate
0.01M Tris buffer
5 mg/ml (w/v) Brij ®-35
 (ICI Americas Inc., Polyoxyethylene
 (23) lauryl ether)
0.2 mg/ml (w/v) dextran sulfate
 (av. mol. wt. 500,00)
pH at 8.2

Components 1, 2 and 3 were combined in a ratio of 1:20 (v/v) as the reagent system. This assay was then performed on an automated bichromatic diagnostic analyzer. 250 microliter aliquots of the reagent system were dispensed into cuvettes that were maintained at 30 deg. C. A 25 microliter sample of each of the ammonia standards containing 0, 1, 2, 4, 6, 8, 10, 12, 14, 16 and 18 micrograms/ml (w/v)of ammonia was immediately dispensed into the individual cuvettes containing the reagent system. 5.6 seconds later an initial spectrophotometric read at 340/560 nm was taken. Three minutes after the initial read, a second spectrophotometric read was taken and the difference in absorbance between the two values was obtained and used to calculate the level of ammonia in each sample.

Figure 2:
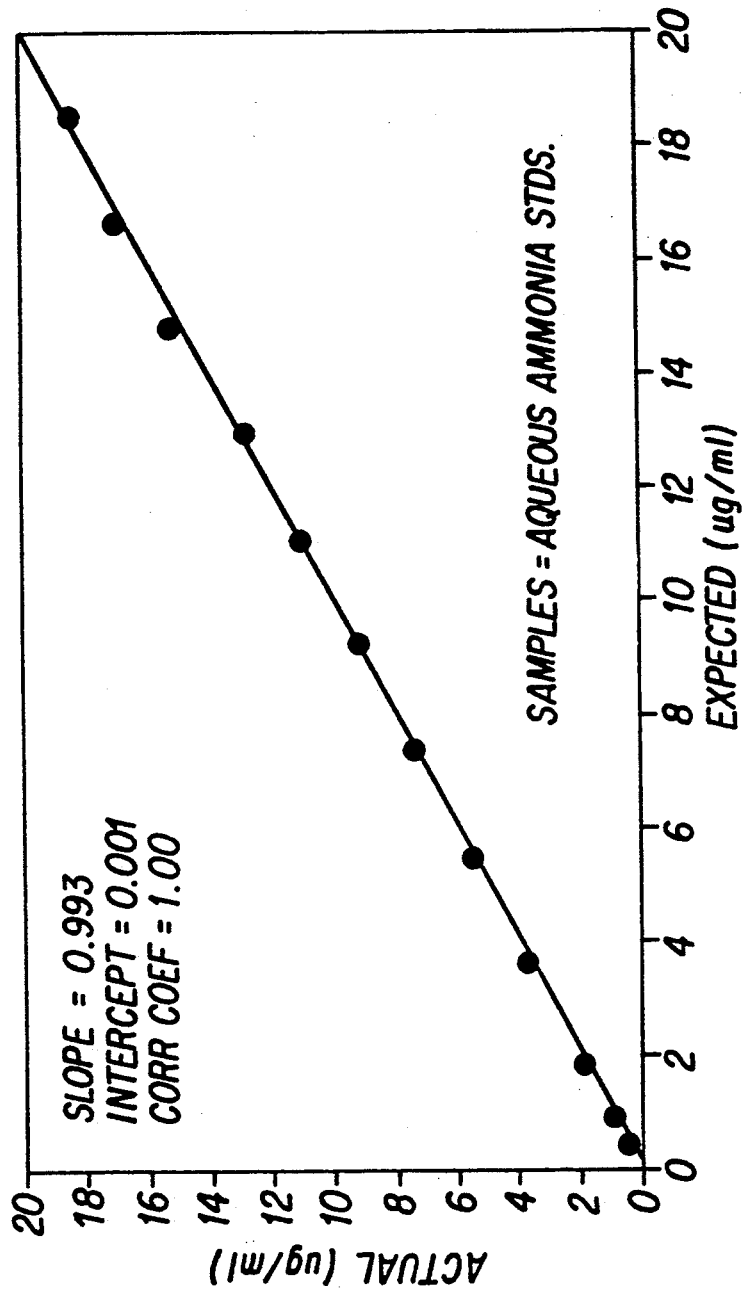

FIG. 2 depicts the results of this assay, showing a correlation coefficient of 1.00 between the expected ammonia values and the actual values obtained in the assay. Also, the slope of the line of FIG. 2 is 0.993, with an intercept of 0.001.

Although the reagents used in Components 1, 2 and 3 were used in the concentrations described, these concentrations may be varied by one skilled in the art to obtain substantially similar results.

EXAMPLE 2

Components 1, 2 and 3 are the same as those in Example 1. 100 microliters of Component 1 are combined with 1 ml of Component 3. 0.5 ml of this mixture is dispensed into each of two cuvettes with a thickness of 1 cm and allowed to equilibrate to 37 deg. C. Next, 0.05 ml of plasma sample is added to one cuvette, and 0.05 ml of water, the reagent blank, is added to the second cuvette. The cuvettes are mixed and the initial absorbance is read at 340 nm Then, 0.05 ml of Component 2 is added to each cuvette and the reaction is allowed to proceed for about three minutes at 37 deg. C. The absorbance is measured again and the difference in absorbance between the two steps is obtained and used to calculate the level of ammonia in each sample.

EXAMPLE 3

Figure 3:
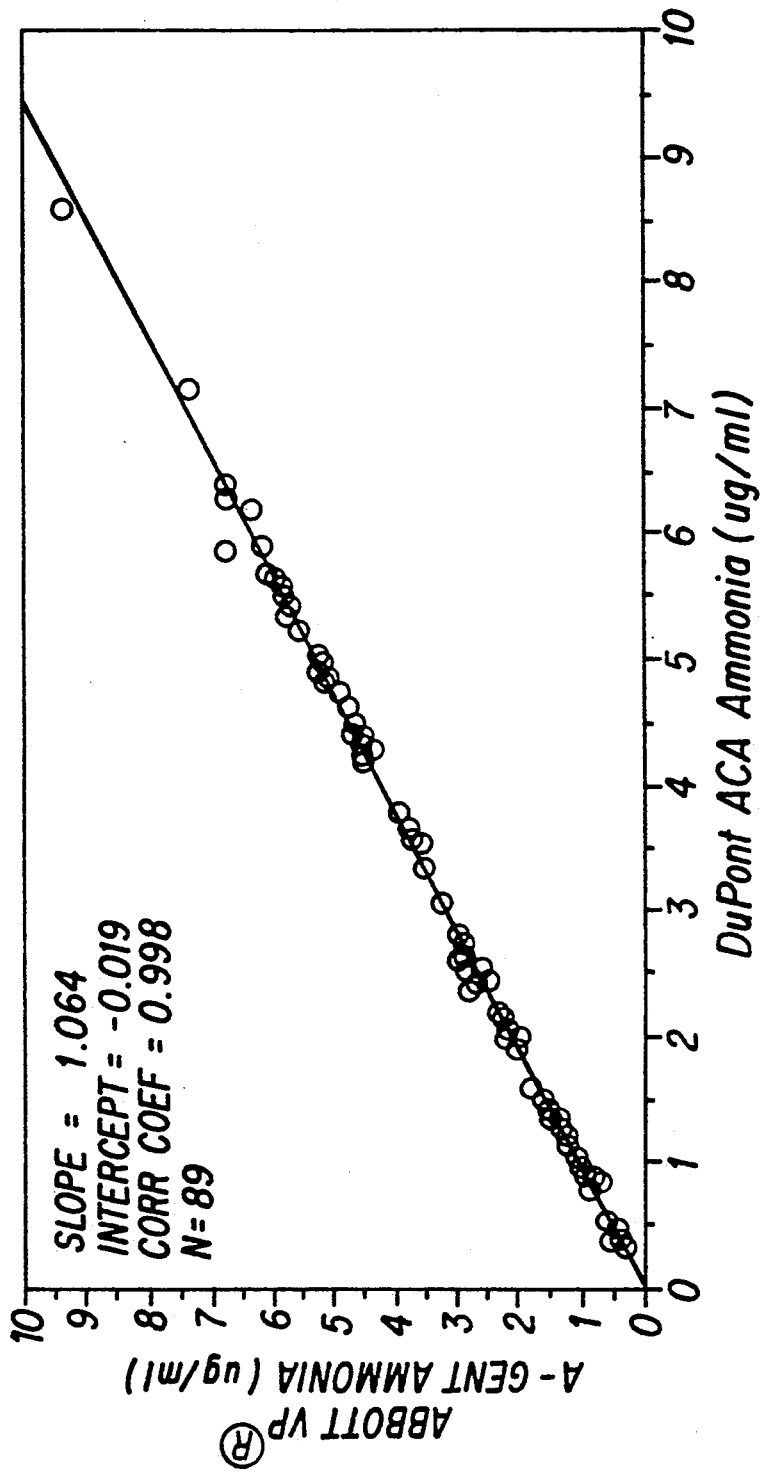

89 plasma samples were measured for ammonia levels the procedure described in Example 1. Concurrently, the same samples were analyzed using the DuPont ACA Ammonia assay method. The DuPont method is known to those skilled in the art as a very accurate method. FIG. 3 shows that the claimed method, when compared to the ACA Ammonia assay, produces test results exhibiting a high degree of correlation.

The results of the ammonia determination for ten representative plasma samples from the total 89 that were run are shown in Table 1 below.

TABLE 1

| Human Plasma Samples | Ammonia levels (ug/ml) | |
| --- | --- | --- |
| | Present Invention | DuPont ACA |
| Sample 1 | 0.34 | 0.34 |
| Sample 2 | 0.54 | 0.48 |
| Sample 3 | 1.38 | 1.31 |
| Sample 4 | 1.33 | 1.27 |
| Sample 5 | 2.00 | 1.92 |
| Sample 6 | 5.86 | 5.59 |
| Sample 7 | 4.53 | 4.26 |
| Sample 8 | 5.93 | 5.65 |
| Sample 9 | 3.95 | 3.78 |
| Sample 10 | 2.48 | 2.45 |

The reagents can be configured in a kit in a number of different ways. They can all be powders which are combined into one container in premeasured amounts and which are then reconstituted with water or a buffer or buffer system to yield a working reagent. Alternatively, the kit can consist of various powder and liquid combinations, which must be mixed to become a working reagent. The kit can also contain the reagents as separate liquids which may be combined by the user or the diagnostic instrument system using this assay. All of the reagents, in any format, may contain appropriate stabilizer or stabilizing systems. The reagents can be packaged into a kit wherein the individual components of the kit are stored separately and combined before use.

An example of a reagent combination in a kit is comprised of three separate compartments, each compartment containing one of the following:

(a) GLDH and alpha-ketoqlutarate in a buffer;
(b) NHxDPH in a buffer; and
(c) Diluent buffer Another way of packaging the reagents in a kit comprises having the GLDH, alpha-ketoglutarate, NHxDPH and the buffer or buffer systems in a powder form wherein all components are premixed into one package. The user could also either be supplied with a diluent buffer or use their own buffer or water to reconstitute the reagent system for use. When combined in predetermined ratios, a working ammonia reagent is formed, and the ammonia assay can be performed with a minimum of time expenditure by the laboratory personnel. An example of the predetermined ratios that can be used for each of the reagents in the kit is a kit containing the following, each in separate compartments:

(a) about 0.01 to about 0.25M phosphate buffer, pH 7 to 7.4; from about 1mM to about 1M alpha-ketoqlutarate; about 100 to about 10,000 U/ml qlutamate dehydrogenase; and glycerol;

(b) approximately 0.5 to about 10mM NHxDPH in an aqueous solution at a pH of approximately 10, and a stabilizer; and (c) about 0.01 to about 0.25 M tris-(hydroxymethyl)-aminomethane buffer at pH of about 8.2 to about 8.6.

We claim:

1. A method for determining the amount of ammonia present in a sample comprising contacting said sample with qlutamate dehydrogenase, alpha-ketoqlutarate and reduced nicotinamide hypoxanthine dinucleotide phosphate and determining therefrom by spectrophotometric means the amount of ammonia present in said sample.

2. A method according to claim 1 wherein said sample is selected from the group consisting of plasma, serum, urine and body fluids.

3. A method according to claim 1 wherein said sample is selected from the group consisting of chemicals and foodstuffs.

4. A method according to claim 1 wherein optionally a stabilizer is present.

5. A method according to claim 4 wherein said stabilizer comprises a mixture of surfactant and dextran sulfate.

6. A method according to claim 4 wherein said stabilizer comprises a mixture of polyoxyethylene lauryl ether and dextran sulfate with an average molecular weight of approximately 500,000.

7. A method for determining the amount of ammonia in a sample comprising:
(a) contacting said sample, qlutamate dehydrogenase, alpha-ketoqlutarate and reduced nicotinamide hypoxanthine dinucleotide phosphate for a time sufficient to consume the ammonia present; and
(b) measuring absorbance change through spectrophotometric means and determining therefrom the amount of ammonia present in said sample.

8. A method according to claim 7 wherein contacting of said sample, glutamate dehydrogenase, alpha-ketoglutarate and reduced nicotinamide hypoxanthine dinucleotide phosphate occurs in a buffered solution, maintaining said solution at a pH in the range from about 6 to about 9.5.

9. A method according to claim 8, wherein the determination is carried out in a buffer in the range of from about pH 6 to about pH 9.5.

10. A method according to claim 8, wherein the determination is carried out in a buffer in the range of from about pH 8 to about pH 9.

11. A method according to claim 8, wherein the determination is carried out in a buffer in the range of from about pH 8.3 to about pH 8.5.

12. A method according to claim 8, wherein the determination is carried out in a buffer of approximately pH 8.4.

13. A method according to claim 8, wherein said buffer comprises a single buffer or a buffer solution.

14. A method for determining the amount of ammonia in a sample comprising:
(a) contacting said sample with alpha-ketoqlutarate and reduced nicotinamide hypoxanthine dinucleotide phosphate;
(b) measuring the initial absorbance;
(c) adding qlutamate dehydrogenase for a time sufficient until substantially all of the ammonia is consumed; and
(d) measuring the final absorbance, calculating the absorbance change between the initial and final absorbance, and determining therefrom the amount of ammonia in said sample.

15. A kit for determining the level of ammonia in a sample comprising:
  (a) qlutamate dehydrogenase and alpha-ketoqlutarate in a buffer;
  (b) reduced nicotinamide hypoxanthine dinucleotide phosphate; and
  (c) diluent buffer;
each of a b, and c being packaged in separate compartments.

16. A kit for determining the level of ammonia in a sample comprising:
  (a) about 0.01 to about 0.25M phosphate buffer, pH 7 to 7.4; from about 1 mM to about 1M alpha ketoqlutarate; about 100 to about 10,000 U/ml glutamate dehydrogenase; and glycerol;
  (b) approximately 0.5 to about 10 mM nicotinamide hypoxanthine dinucleotide phosphate in an aqueous solution at a pH about 10, and stabilizer; and
  (c) about 0.01 to about 0.25 M tris-(hydroxymethyl)aminomethane buffer at pH of about 8.2 to about 8.6;
each of a, b, and c packaged in separate compartments.

17. A kit for determining the level of ammonia in a sample comprising:
  (a) approximately 16 mg/ml alpha ketoqlutarate, about 572 U/ml qlutamate dehydrogenase, about 0.05M phosphate buffer at a pH from about 7.0 to 7.4, about glycerol (v/v), about 0.05 mg/ml bovine gamma lobulin, and about 0.5 mg/ml sodium azide;
  (b) about 4 mg/ml nicotinamide hypoxanthine dinucleotide phosphate, about 50% propylene glycol, about 1 mg/ml sodium azide, about 3.1 mg/ml boric acid, approximately 16 mg/ml bicine buffer, at a pH of approximately 10.2; and
  (c) about 0.01M Tris buffer, about 5 mg/ml polyoxyethylene lauryl ether, about 0.2 mg/ml dextran sulfate with an average molecular weight of about 500,000, at a pH of approximately 8.2;
each of a, b, and c is packaged in a separate compartment.

18. A kit for determining the level of ammonia in a sample comprising combining the powdered components of qlutamate dehydrogenase, alpha-ketoqlutarate, reduced nicotinamide hypoxanthine dinucleotide phosphate and buffer in effective amounts in one package.

* * * * *